US009492475B2

(12) United States Patent
Castro Feo et al.

(10) Patent No.: US 9,492,475 B2
(45) Date of Patent: Nov. 15, 2016

(54) ANTIOXIDANT COMPOSITION

(75) Inventors: Maria Begoña Castro Feo, Leioa (ES); Iker Azcoitia Ramsden, Bilbao (ES); Teodoro Palomares Casado, Vitoria (ES); Jone Herrero De Miguel, Sopelana (ES); Ana Isabel Alonso Varona, Getxo (ES); Maite Del Olmo Basterrechea, Sopelana (ES)

(73) Assignee: HISTOCELL, S.L., Derio (Bizkaia) (ES)

( * ) Notice: Subject to any disclaimer, the term of this patent is extended or adjusted under 35 U.S.C. 154(b) by 0 days.

(21) Appl. No.: 13/704,207

(22) PCT Filed: Jun. 14, 2011

(86) PCT No.: PCT/ES2011/070427
§ 371 (c)(1),
(2), (4) Date: Dec. 13, 2012

(87) PCT Pub. No.: WO2011/157880
PCT Pub. Date: Dec. 22, 2011

(65) Prior Publication Data
US 2013/0095049 A1 Apr. 18, 2013

(30) Foreign Application Priority Data

Jun. 15, 2010 (EP) .................................... 10165939

(51) Int. Cl.
| *A61K 8/00* | (2006.01) |
| *A61K 8/18* | (2006.01) |
| *A61Q 17/04* | (2006.01) |
| *A61K 31/736* | (2006.01) |
| *A61K 31/12* | (2006.01) |
| *A61K 31/198* | (2006.01) |
| *A61K 36/483* | (2006.01) |
| *A61K 36/9066* | (2006.01) |
| *A61K 35/33* | (2015.01) |
| *A61K 8/73* | (2006.01) |
| *A61K 35/12* | (2015.01) |
| *A61K 35/30* | (2015.01) |
| *A61K 35/32* | (2015.01) |
| *A61K 35/36* | (2015.01) |
| *A61Q 19/00* | (2006.01) |

(52) U.S. Cl.
CPC ............ *A61K 31/736* (2013.01); *A61K 8/737* (2013.01); *A61K 31/12* (2013.01); *A61K 31/198* (2013.01); *A61K 35/12* (2013.01); *A61K 35/30* (2013.01); *A61K 35/32* (2013.01); *A61K 35/33* (2013.01); *A61K 35/36* (2013.01); *A61K 36/483* (2013.01); *A61K 36/9066* (2013.01); *A61Q 19/00* (2013.01)

(58) Field of Classification Search
CPC ............ A61K 8/44; A61K 8/97; A61K 8/737; A61K 31/715; A61K 31/736; A61K 47/36; A61K 31/12; A61K 31/198; A61K 35/12; A61K 35/30; A61K 35/33; A61K 35/36; A61K 36/483; A61K 36/9066; A61Q 17/04; A61Q 19/00; A61Q 19/08
See application file for complete search history.

(56) References Cited

U.S. PATENT DOCUMENTS

| 5,804,213 A | 9/1998 | Rolf |
| 6,406,712 B1 | 6/2002 | Rolf |
| 2003/0103933 A1* | 6/2003 | Brody et al. ................. 424/85.1 |
| 2006/0104931 A1* | 5/2006 | Fukutome et al. ......... 424/70.13 |
| 2006/0286046 A1* | 12/2006 | Haber ............................. 424/59 |

FOREIGN PATENT DOCUMENTS

| EP | 0 781 550 A1 | 12/1996 |
| EP | 0 792 653 A2 | 2/1997 |
| EP | 0 848 951 A1 | 12/1997 |
| JP | H10-53517 | 2/1998 |
| JP | 2002-080338 | 3/2002 |
| JP | 2006-500129 | 1/2006 |
| WO | WO-9925395 A2 | 5/1999 |
| WO | WO-0149258 A1 | 7/2001 |
| WO | WO 2004/029230 | 4/2004 |
| WO | WO-2004112850 A1 | 12/2004 |
| WO | WO-2005049101 A1 | 6/2005 |
| WO | WO-2005084650 A1 | 9/2005 |
| WO | WO-2009137827 A2 | 11/2009 |

OTHER PUBLICATIONS

Sharma RA et al. 2005. Curcumin: The story so far. European Journal of Cancer; 41: 1955-1968.*
Thaakur, Santh Rani, et al. "Effect of N-Acetyl Cysteine on Wound Healing," Pharmacologyonline, vol. 1 (2009) pp. 369-376.
Panchatcharam, Manikandan, et al., "Curcumin improves wound healing by modulating collagen and decreasing reactive oxygen species," Molecular and Cellular Biochemistry, vol. 290 (2006) pp. 87-96.
International Search Report issued on Oct. 25, 2011 in Priority International Patent Application No. PCT/ES2011/070427 (WO2011/157880A1).
Gopinath, D., et al., "Dermal wound healing processes with curcumin incorporated collagen films," Biomaterials 25 (2004) pp. 1911-1917.

(Continued)

*Primary Examiner* — Johann R Richter
*Assistant Examiner* — David Browe
(74) *Attorney, Agent, or Firm* — Jenkins, Wilson, Taylor & Hunt

(57) ABSTRACT

The present invention relates to an antioxidant composition comprising a combination of galatomannan and N-acetyl cysteine for its use in the treatment of a skin disease or condition resulting from reactive oxygen species production in the skin or involving reactive oxygen species production in the skin, to a hydrogel containing said combination as well as to dressing wounds comprising said hydrogel and its use in the healing of ulcers, wounds, burns and scalds.

2 Claims, 7 Drawing Sheets

(56) References Cited

OTHER PUBLICATIONS

Al-Jawad et al., "Role of Antioxidants in the Treatment of Burn Lesions," Annals Burns Fire Disasters, vol. XXI, No. 4, pp. 186-191 (2008).

James et al., "Evidence of oxidative stress in chronic venous ulcers," Wound Repair Generation, vol. 11, pp. 172-176 (2003).

Pinnell, "Cutaneous photodamage, oxidative stress, and topical antioxidant protection," J. Am. Acad. Dermatol., vol. 48, pp. 1-22 (2003).

Pourzand et al., "Apoptosis, the Role of Oxidative Stress and the Example of Solar UV Radiation," Photochemistry Photobiology, vol. 70, pp. 380-390 (1999).

Sander et al., "Role of oxidative stress and the antioxidant network in cutaneous carcinogenesis," International Journal Dermatology, vol. 43, pp. 326-335 (2004).

Scharstuhl et al., "Curcumin-induced fibroblast apoptosis and in vitro wound contraction are regulated by antioxidants and heme, oxygenase: implications for scar formation," J. Cell Mol. Med., vol. 13, pp. 712-725 (2009).

Trommer et al., "The examination of polysaccharides as potential antioxidative compounds for topical administration using a lipid model system," International Journal of Pharmaceutics, vol. 298, pp. 153-163 (2005).

Zhou et al., "Oxidative stress in the pathogenesis of psoriasis" Free Radical Biology Medicine, vol. 47, pp. 891-905 (2009).

\* cited by examiner (a)

(b)

(a)

(b)

★ Significant differences with respect to the oxidation control
● Significant differences with respect to NAC, Tur, NAC+Tur and LBG+Tur treatments
▲ Significant differences with respect to any of the treatments (a)  (b)

(c)  (d)

ANTIOXIDANT COMPOSITION

CROSS-REFERENCE TO RELATED APPLICATIONS

This application is filed under the provisions of 35 U.S.C. §371 and claims the priority of International Patent Application No. PCT/ES2011/070427 filed on Jun. 14, 2011, and of European Patent Application No. EP10165939.9 filed on Jun. 15, 2010. The disclosures of the foregoing international patent application and European patent application are hereby incorporated by reference herein in their respective entireties.

FIELD OF THE INVENTION

The present invention relates to antioxidant compositions and their use in the treatment of diseases, disorders and conditions affecting the skin, particularly skin conditions that involve the production of reactive oxygen species in human skin, such as photoaging and other age-related skin damage. It also refers to wound dressings and particularly to compositions for delivery active agents to wounds.

BACKGROUND

The aging of the population and the increase of chronic metabolic diseases such as hypertension or diabetes has favored the presence of chronic ulcers in recent years.

Occasionally, due to the health condition of the patient (diabetes) or to the presence of a large amount of damage in the tissue (serious burns), phenomena can arise which alter the series of processes which must take place for healing to occur, developing a chronic ulcer.

The formation of a chronic ulcer is associated with an excessive inflammatory process which alters the synthesis of the signaling molecules involved in regulating the process taking place in healing. Recent studies directly relate the physiopathology of chronic ulcers with the oxidative stress present in the bed of the wound, as a consequence of the proinflammatory environment of the lesioned area.

When oxidative stress occurs, the organism has detoxification mechanisms capable of control the excess of the reactive oxygen species generated, in contrast, when there is a lack of adjustment between the detoxificant capacity of the organism and the free radicals present in the bed of the wound, the healing process slows down, giving rise to a chronic ulcer.

A lack of adjustment in the detoxification mechanisms of reactive oxygen metabolites is one of the main causes of chronicity in ulcers.

The healing of chronic wounds may be induced by the use of antioxidant wound dressings that react specifically with excess reactive oxygen species and hence reduce the level of oxidative stress. In the art, different examples of materials for healing purposes are described.

For example, in U.S. Pat. No. 6,406,712, a wound dressing material has been described, which is formed by mixing dry hydrocolloid polymer powder with water contained in a sealed package having a temporary or manually-removable barrier so that the dry polymer and water can be stored separately from each other while in the package.

Another description, at the patent application WO 01/49258A2, comprises tissue contact materials, such as biocompatible polymer comprising a non-gellable polysaccharide, such as guar gum, that entrap oxygen within closed cell foam-like material capable of providing or maintaining optimal oxygen tension at a compromised tissue site while absorbing excess fluid and optimizing the microenvironment to facilitate tissue repair and regeneration if needed.

The patent application EP0781550A1, describes a bioadhesive pharmaceutical composition for the controlled liberation of active ingredients, antiulcer among others, constituted by a co-polymer of vinyl acetate and polyvinylpyrrolidone and an additional component, such as the locust bean gum among others.

The antioxidant activity of galactomannans upon reducing the lipid peroxidation of systems subjected to UVA radiation has also recently been described. Their capacity to increase the elasticity of different mixtures of hydrogels and their capacity to absorb water, being able to provide the bed of the wound with the necessary degree of moisture needed by the healing process, are also known.

The international application WO2005/084650A1 claims a storage stable and dry active ingredient delivery system for pharmaceutically active ingredients for dermal use with wound healing purposes. The delivery system comprises a xerogel in that the gel-forming material is a polysaccharide, for example galactomannan derivatives. When the xerogel comes into contact with fluids it is rehydratated and forms a hydrogel, whereby the applied active ingredients are dissolved and released at a controlled rate from the hydrogel leading to a locally high concentration.

Solid, bioabsorbable materials for use as wound dressings are described at the patent application EP0792653, where such a solid is formed by a mixture of xanthan, and at least one galactomannan, such as guar gum or locust bean gum. The material also comprises therapeutic agents among which are particularly preferred those that actively promote wound healing such as glicosaminoglycans.

In a similar procedure as described above a wound dressing with healing purposes is claimed by the international application WO99/25395, where the matrix comprises a biocompatible cross-linked polymer and a non-gellable polysaccharide, a galactomannan, which includes as well one or more active ingredients, for example, wound healing agents like growth factors, mucopolysacharides and proteins.

Other types of wound healing dressings are described by the international applications WO2004/112850 and WO2005/049101 where generally the material is formed by a bioabsorbable substrate, which could be galactomannan, dyed with an antioxidant dyestuff, which can react with oxygen reactive species, reducing, in that way, the level of oxidative stress at the wound.

N-acetyl cysteine is also known as an antioxidant molecule which acts by increasing the synthesis of intracellular glutatión (GSH). The reducing effect of GSH contributes to directly eliminating the reactive oxygen species and also to recycling already used antioxidants. Its use in chronic ulcers would reduce the oxidative stress thereof, thus favoring their healing (Manikandan, P. et al, *Molecular and Cellular Biochemistry*, 2006, 290, 87-96; Rani Thaakur, S. et al, *Pharmacologyonline*, 2009, 1, 369-376).

The antioxidant activity of curcumin is also known. Curcumin is the purified state of the raw extract of Turmeric root, a plant mostly cultivated in Southeast Asia and widely used in traditional medicine for the treatment of skin-related diseases. Gopinath, D. (Biomaterials, 2004, 25, 1911-1917) demonstrates the improved capacity of wound healing by curcumin antioxidant when it is incorporated to a collagen matrix, which also acts as a supportive matrix for the regenerative tissue.

Although the antioxidant properties of galactomannans and N-acetyl cysteine are well-documented in the prior art, there is no indication about the particular advantages conferred by the combination of both components, and particularly, to the antioxidant synergistic effect provided on cells cultures suffering extensive oxidative stress.

BRIEF DESCRIPTION OF THE INVENTION

The authors of the present invention have found that the combination of galactomannan and N-acetyl cysteine provides a synergistic effect in the antioxidant capacity of both components, which results in an unexpected advantage for its use in the treatment of diseases or disorders resulting from reactive oxygen species production in the skin of a subject or diseases or conditions which involves the reactive oxygen species production in the skin of a subject.

The experimental tests have shown that human skin cells (fibroblasts) subjected to an oxidative stress undergo an increase in the cell survival capacity/preservation when a combination of galactomannan, such as locust bean gum, and N-acetyl cysteine is administered to the culture cells.

Additional experiments have also revealed that said combination provides a significant reduction in the intracellular levels of reactive oxygen metabolites in fibroblast cell cultures subjected to an oxidative stress in the presence of oxygen peroxide, when compared to locust bean gum or N-acetyl cysteine alone.

Furthermore, an even higher synergistic effect has been observed when curcumin (or turmeric) is added to the combination of galactomannan and N-acetyl cysteine.

Therefore, in a first aspect the present invention refers to an antioxidant composition comprising galactomannan and N-acetyl cysteine for its use in the therapeutic or prophylactic treatment of a skin disease or condition resulting from reactive oxygen species production in the skin of a subject or of a skin disease or condition which involves the reactive oxygen species production in the skin of a subject.

Particularly preferred is the use of locust bean gum as galactomannan in the composition used in the invention.

In a particular embodiment, the antioxidant composition as defined above further comprises curcumin (turmeric) as an additional antioxidant ingredient.

The invention also relates to a method for the therapeutic or prophylactic treatment of a skin disease or condition resulting from reactive oxygen species production in the skin of a subject or of a skin disease or condition which involves the reactive oxygen species production in the skin of a subject, which comprises the administration of a therapeutically effective amount of a composition comprising galactomannan and N-acetyl cysteine.

Another aspect of the present invention relates to an antioxidant composition which comprises galactomannan, N-acetyl cysteine and curcumin.

Another aspect of the present invention relates to the antioxidant composition as defined above for its use as a medicament.

Another aspect of the invention refers to a hydrogel which comprises galactomannan and N-acetyl cysteine, wherein the galactomannan is in the form of a cross-linked matrix, and N-acetyl cysteine is incorporated in said cross-linked matrix of galactomannan. In a particular embodiment, the galactomannan is cross-linked by means of a cross-linking agent, preferably the cross-linking agent is glutaraldehyde.

In another aspect, the invention relates to the hydrogel as defined above, wherein the galactomannan matrix further comprises curcumin incorporated therein.

Additionally, the present invention also refers to the hydrogel as defined above which further includes cells. Particularly preferred are cells selected from the group consisting of fibroblasts, keratinocytes, endothelial cells, differentiated or undifferentiated mesenchymal stem cells, corneal cells, epithelial cells, cells from leucocitary system, cells from hematopoietic system, differentiated or undifferentiated stem cells, chondrogenic cells, osteoblasts, miocytes, adipocytes and neurons or other cells from the peripheric or central nervous system.

An additional aspect of the present invention refers to a process for the preparation of a hydrogel as defined above which comprises:
  a) dissolving the galactomannan in an aqueous solution;
  b) subjecting the galactomannan to a chemical cross-linking by adding a cross-linking agent to the aqueous solution of galactomannan to obtain a hydrogel comprising a cross-linked glucomannan matrix;
  c) incorporating N-acetyl cysteine, and optionally the curcumin, into the cross-linked glucomannan matrix.

Another aspect of the present invention refers to a wound dressing comprising the hydrogel as defined above.

An additional aspect of the present invention relates to a hydrogel as defined above for its use as a medicament.

Another aspect of the invention refers to a hydrogel as defined above for its use in the treatment and/or healing of acute surgical and traumatic wounds, burns, scalds, fistulas, venous ulcers, arterial ulcers, pressure sores (otherwise known as decubitus ulcers), diabetic ulcers, ulcers of mixed aetiology, and other chronic or necrotic wounds and inflammatory lesions and disorders.

An additional aspect of the invention relates to cosmetic composition which comprises galactomannan and N-acetyl cysteine.

In another aspect, the invention relates to the cosmetic composition as defined above, which further comprises curcumin.

Another aspect of the present invention refers to the use of a cosmetic composition as defined above for the treatment of an age-related skin damage.

Another aspect of the present invention refers to the use of a cosmetic composition as defined above as an UV-radiation protector.

DETAILED DESCRIPTION OF THE INVENTION

Figure 1:
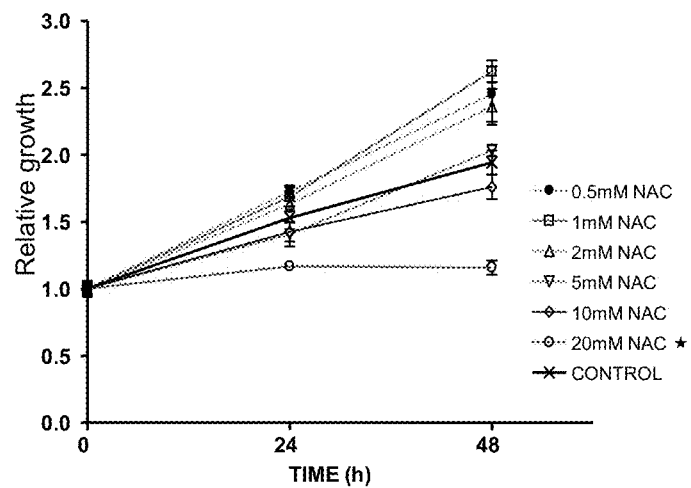
FIG. 1 shows: (a) the results of cell proliferation in fibroblasts by means of the MTT colorimetric assay, using different concentrations of NAC, and (b) the $IC_{50}$ values with respect to the control.
Figure 1:
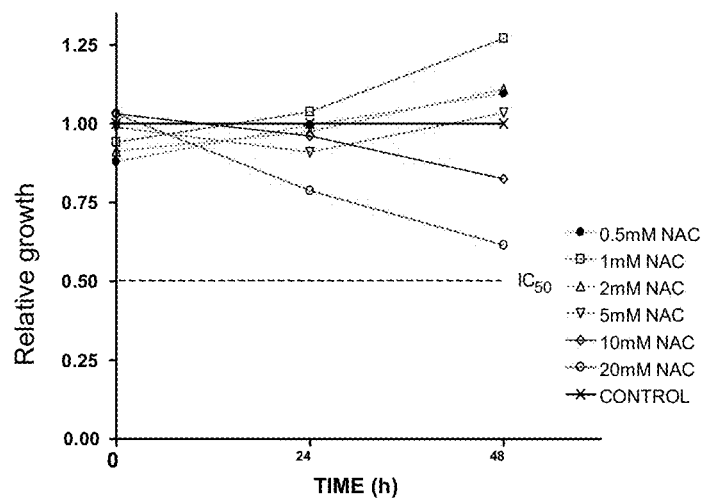

The antioxidant composition used in the invention comprises two antioxidant agents, namely a galactomannan and N-acetyl cysteine. These components are physically mixed in the composition without being bonded by any chemical bond or interaction.

As shown in the experimental tests, the combination of a galactomannan, such as carob locust bean gum, and N-acetyl cysteine provides an antioxidant synergistic effect over fibroblast cell cultures subjected to an oxidative stress, improving the cell survival capacity while reducing the intracellular levels of reactive oxygen metabolites.

Galactomannans are polysaccharides containing a mannose backbone with galactose side groups, more specifically a (1-4)-linked betha-D-mannopyranose backbone with branch points from their 6 positions linked to alpha-D-galactose, i.e. 1-6 linked alpha-D-galactopyranose. Galactomannan gums include locust bean gum (LBG), guar gum, cassia gum, tara gum, mesquite gum, and fenugreek gum.

In a particular embodiment, the galactomannan is selected from the group consisting of guar gum, locust bean gum, cassia gum, tara gum, mesquite gum, fenugreek gum and white clover bean gum. More preferably, the galactomannan is locust bean gum. Locust bean gum is a galactomannan polysaccharide consisting of mannopyranose backbone with branchpoints from their 6-positions linked to α-D-galactose residues. Locust bean gum has about 4 mannose residues for every galactose residue (a mannose/galactose ratio of about 4).

Galactomannans may be derived from recombinant or synthetic sources. For example, galactomannose may be synthesized in vivo from GDP-mannose and UDP-galactose by the enzymes mannan synthase and galactosyltransferase. DNA coding for these proteins has been isolated and characterized, (US Publication 2004/0143871) and recombinant plants transformed with these enzymes have been shown to express elevated levels of galactomannan. In addition, the degree of galactosylation of the mannopyranose backbone may be influenced by the presence (or absence) of alpha-galactosidase in vivo, (see Edwards et al. Plant Physiology (2004) 134: 1153-1162). Alpha-galactosidase removes galactose residues from the mannopyranose backbone. For example, seeds that naturally express galactomannans with a lower degree of galactosylation may express (or express more) alpha galactosidase, which removes galactose moieties from the mannopyranose backbone in those species of plant. The alpha-galactosidase enzyme may be used to reduce the presence of galactose on the mannopyranose backbone of naturally occurring galactomannose gums in a laboratory manipulation of the characteristics of the naturally occurring galactomannose gum. Embodiments of the present invention include galactomannans, which have been treated with alpha-galactosidase to reduce the presence of galactose on the mannopyranose backbone. Embodiments of the present invention include galactomannan gums which have been treated with alpha-galactosidase or other enzymes or chemical treatments, to "tune" the gums to provide the gum with desired characteristics as cell culture surfaces.

The weight proportion of galactomannan in the composition of the invention ranges from 1 to 5% with respect to the total weight of the composition.

N-acetyl cysteine is an antioxidant molecule which intervenes in the synthesis of intracellular glutathione, a compound which contribute to directly eliminate the free oxygen radicals in the cell, as well as to recycle antioxidants already used.

The N-acetyl cysteine is preferably present in the composition of the invention in a concentration that ranges from 1 to 10 mM, more preferably from 1 to 5 mM.

In a preferred embodiment, the antioxidant composition used in the invention is suitable for topical application on the skin. The topical antioxidant compositions may take any of a wide variety of forms, and include, for example dressings, lotions, solutions, sprays, creams, gels, ointments, or the like.

Lotions are preparations to be applied to the skin surface without friction, and are typically liquid or semi-liquid preparations in which solid particles, including the active ingredients, are present in a water or alcohol base. Lotions are usually suspensions of solids, and preferably comprise a liquid oily emulsion of the oil-in-water type. Lotions are preferred formulations for treating large body areas because of the ease of applying a more fluid composition. It is generally preferred that that the insoluble matter in a lotion (hydrogel) be finely divided. Lotions contain from about 0.001% to about 30% of the active ingredients, from 1% to 25% of an emollient and the appropriate amount of water. Examples of emollients are hydrocarbon waxes and oils such as mineral oils, petrolatum, paraffin, ceresin, microcrystalline wax, polyethylene and perhydrosqualene; silicone oils such as dimethylpolysiloxanes, methylphenylpolysiloxanes and water-soluble and alcohol-soluble glycol-silicone copolymers; triglycerides, such as animal and vegetable fats and oils; alkyl esters of fatty acids having 10 to 20 carbon atoms, alkenyl esters of fatty acids having 10 to 20 carbon atoms; fatty acids having 10 to 20 carbon atoms, such as pelargonic, lauric, myristic, palmitic, stearic, isostearic, hydroxystearic, oleic, linoleic, ricinoleic, arachidonic, behenic and erucic acids; fatty alcohols having 10 to 20 carbon atoms, such as lauryl, myristoyl, palmitoyl, stearyl, isostearyl, hydroxystearyl, oleyl, ricinoleyl, behenyl, erucyl and 2-octyl dodecanol alcohols are appropriate examples of fatty alcohols; fatty alcohol ethers, such as ethoxylated fatty alcohols having 10 to 20 carbon atoms including lauryl, cetyl, stearyl, isostearyl, oleyl and cholesterol alcohols having attached thereto from 1 to 50 ethylene oxide groups or 1 to 50 propylene oxide groups; lanolin and derivatives; waxes such as beeswax, spermaceti, myristoyl myristate and stearyl stearate; beeswax derivatives, such as polyoxyethylene sorbitol beeswax; vegetable waxes, including, but not limited to, carnauba and candelilla waxes; phospholipids such as lecithin and derivatives; sterols, such as cholesterol and acyl esters of cholesterol; and amides, such as fatty acid amides, ethoxylated acyl amides and solid fatty acid alkanolamides.

The lotions of the invention would further contain from 1% to 30% of an emulsifier. The emulsifiers can be anionic, cationic or non-ionic. Examples of non-ionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbons in the alkyl chain condensed with 2 to 20 moles of ethylene oxide, mono- and di-acyl esters of ethylene glycol, wherein the fatty acid contains from 10 to 20 carbons, monoglycerides wherein the fatty acid contains from 10 to 20 carbons, diethylene glycol, polyethylene glycols of molecular weight 200 to 6000, polypropylene glycol of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, fatty acids saponified (soaps) with potassium, sodium, or triethanolamine, wherein the fatty acid contains from 10 to 20 carbons. Other suitable anionic emulsifiers include, but are not limited to, alkali metals, ammonium or substituted ammonium with alkyl sulfates, alkyl arylsulfonates and alkyl ethoxy ether sulfonates having 10 to 30 carbons in the alkyl chain and from 1 to 50 ethylene oxide units. Suitable cationic emulsifiers include quaternary ammonium and morpholinium and pyridinium compounds.

The balance of the composition is water. The lotions are formulated by simply admixing all of the components together. Preferably, the active ingredients are dissolved in the emollient and the resulting mixture is added into the water.

The compositions of the present invention may also be formulated in the form of a solution. Solutions are homogenous mixtures prepared by dissolving the active ingredients in a liquid such that the molecules of the dissolved ingredients are dispersed among those of the solvent. Solutions contain from 0.001% to 30% of the antioxidant active ingredients and the adequate amount of an organic solvent. Organic substances useful as the solvent are propylene glycol, polyethylene glycol, polypropylene glycol, glycerine, sorbitol esters, 1,2,6-hexanetriol, ethanol, isopropanol, diethyl tartrate, butanediol, and mixtures thereof. Such solvent systems can also contain water.

These compositions are applied on the skin in the form of a solution, or solutions are formulated in the form of aerosol and applied on the skin as a spray.

Compositions in the form of aerosol additionally contain from 25% to 80% of a suitable propellant. Examples of propellants include, but are not limited to chlorinated, fluorinated and fluorochlorinated low molecular weight hydrocarbons. Nitrous oxide and carbon dioxide are also used as propellant gases. Enough quantity to expel the content of the cartridge is used.

The composition of the present invention may be also formulated in the form of a cream. For instance, creams, as is well known in the arts of pharmaceutical and cosmetic formulations, are viscous liquids or semisolids emulsions, either oil-in-water or water-in-oil. Cream bases are water-washable, and contain an oil phase, an emulsifier, and an aqueous phase. The oil phase is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant and can be selected from emulsifiers mentioned above for lotions or mixtures thereof.

Gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred organic macromolecules, i.e. gelling agents, may be chemically crosslinked polymers such as crosslinked acrylic acid polymers, for instance the "carbomer" family of polymers, e.g., carboxypolyalkylenes, that may be obtained commercially under the Carbopol® trademark. Also preferred may be hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methyl cellulose and methyl cellulose; gums such as tragacanth and xanthan gum; sodium alginate; and gelatin.

Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. Ointment bases may be grouped in four classes: oleaginous bases, emulsifiable bases, emulsion bases and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil emulsions or oil-in-water emulsions, and include, for example, cetyl alcohol, glyceryl monostearate, lanolin, and stearic cid. Preferred water soluble ointment bases are prepared from polyethylene glycols of varying molecular weight.

A pharmaceutical acceptable vehicle may also be incorporated in the compositions and may be any vehicle conventionally used in the art. Examples include water, lower alcohols, higher alcohols, polyhydric alcohols, monosaccharides, disaccharides, polysaccharides, hydrocarbon oils, waxes, fatty acids, silicone oils, nonionic surfactants, ionic surfactants, silicone surfactants, and water-based mixtures and emulsion-based mixtures of said vehicles.

Topical compositions described above may be applied regularly to whatever skin area that requires treatment with the frequency and in the amount necessary to achieve the desired results. The frequency of treatment depends on the nature of the skin disease or condition, i.e. a skin disease or condition that results from ROS production in skin, as well as the degree of damage or deterioration of the skin.

Due to the antioxidant properties of the combination of galactomannan and N-acetyl cysteine, it can be used to treat or prevent a skin disease or condition that results from reactive oxygen species production in the skin of a subject, or of a skin disease or condition which involves the reactive oxygen species production in the skin of a subject, particularly in skin fibroblasts and keratinocytes.

This treatment includes contacting the skin of a subject by directly applying to the skin a topical formulation as herein described, in a manner that affects the subject, and/or skin tissue in the subject and/or one or a plurality of cells, to obtain a desired pharmacologic effect and/or physiologic effect. The effect may be prophylactic in terms of completely or partially preventing a disease or disorder such as a condition that results from reactive oxygen species production in skin or that involves reactive oxygen species production in skin, or a sign or symptom thereof, and/or the effect may be therapeutic in terms of relieving symptoms or signs or providing a partial or complete cure for such a disorder or disease and/or substantially impairing an adverse effect attributable to the disorder or disease.

Related embodiments, contemplate, by way of example:
  (i) preventing the disease or disorder (e.g., skin condition that results from oxygen reactive species production or that involves oxygen reactive species production) from occurring in a subject that may be predisposed to the disease or disorder, but has not yet been diagnosed as having it;

(ii) inhibiting the disease or disorder, i.e., arresting its progression; or (iii) relieving or ameliorating the disease or disorder, i.e. causing regression.

In a particular embodiment, the treatment of a skin disease or condition that results from the production of reactive oxygen species includes the repair and regeneration of damaged or injured tissue or cells at a site of skin damage. This damage can be the result of the exposure of the subject to a source of oxidative stress that may promote radical oxygen species production in skin, such as sunlight radiation (photodamage), chemical agents (including other topical agents such as medical, pharmaceutical or cosmetic compounds), radiotherapy or chemotherapy. It also includes prophylactic treatments to prevent such damage, for instance, prior to exposure of the subject to a source of oxidative stress that may promote radical oxygen species production in skin, such as UV radiation, chemical agents (including other topical agents such as medical, pharmaceutical or cosmetic compounds) or prior to radiotherapy or chemotherapy.

More particularly, the skin disease or condition results from the exposure to sunlight, more specifically to the UV radiation of type UVA, UVB and UVC. Conditions directly or indirectly a consequence of (or are exacerbated by, or include as a risk factor) exposure to such radiation include both direct and immediate effects, as well as longer term effects, and complications and sequellae that arise from the direct damage, over a longer term.

It is thought that UV radiation impacts skin through both direct and indirect mechanism. The direct damage is that which is incurred upon immediate exposure to radiation, whereas the indirect effects include those which follow the generation of damaged biological molecules and the generation of highly reactive oxygen species which then set other biological and pathological processes in motion. The reactive oxygen species may have deleterious effects in the immediate locale where they are generated, as in the skin, or at distant sites, where such reactive species may have broader systemic effects, as may manifest in what is termed "oxidative stress". An intervention that effectively reduces the level of reactive species, thereby having an anti-oxidant effect, thus may have slow, ameliorate, or stop the progression of a broad range of diseases.

Health problems associated with exposure to UV radiation involve conditions or diseases of the skin, but more widespread and systemic conditions may also arise, or be a part of complications that follow on as a consequence of such conditions or diseases of the skin. Accordingly, such conditions, collectively, may include sunburn, photosensitivity, immunosuppression, premature aging, psoriasis, several types of skin cancer and various immunologiclal diseases, as well as localized or widespread inflammation, various bacterial or fungal infections, skin rashes, and systemic oxidative stresses caused by UV radiation exposure and diet. Actinic keratosis, for example, is a precancerous lesion developed after many years of sun exposure. Polymorphic light eruption, for example, is a rash induced by sunlight exposure, which is understood as involving skin-localized allergy. Types of skin cancer linked to sunlight exposure include, in order of increasing seriousness, basal cell cancer, squamous cell cancer, and malignant melanoma.

In another particular embodiment, the skin disease or condition which involves the reactive oxygen species production in the skin of a subject is selected from acute surgical and traumatic wounds, burns, scalds, fistulas, venous ulcers, arterial ulcers, pressure sores (otherwise known as decubitus ulcers), diabetic ulcers, ulcers of mixed aetiology, and other chronic or necrotic wounds and inflammatory lesions and disorders.

In a particular embodiment of the present invention, the antioxidant composition of the invention further comprises curcumin as an additional active ingredient. It has been found that the combination of galactomannan with N-acetyl cysteine and curcumin provides an even higher synergistic antioxidant effect as shown the examples provided in the present application.

Cucumin, also known as turmeric, is a naturally occurring o-methoxyphenol derivative of formula:

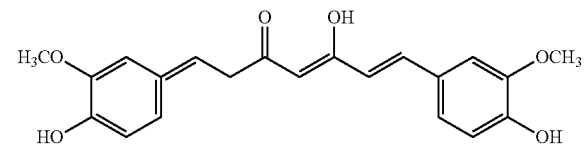

It is a yellow pigment obtained from the rizhomes of *Curcuma Longa* and it has been used for centuries in indigenous medicine for the treatment of a variety of inflammatory conditions. Curcumin also acts as a free radical scavenger and antioxidant, inhibiting lipid peroxidation and oxidative DNA damage.

The curcumin is preferably present in the composition of the invention in a concentration ranging from 1 to about 7.5 μM, more preferably from 1 to 5 μM.

Therefore, another aspect of the present invention refers to an antioxidant composition which comprises glactomannan, N-acetyl cysteina and curcumin.

Said antioxidant composition is also suitable for topical application on the skin and may take any of a wide variety of forms, including, for example dressings, lotions, solutions, sprays, creams, gels, ointments, or the like, such as those mentioned above.

Additionally, the present invention relates to the antioxidant composition which comprises glactomannan, N-acetyl cysteine and curcumin for its use as a medicament.

This antioxidant composition can also be used to treat or prevent a skin disease or condition that results from reactive oxygen species production in the skin of a subject or a skin disease or condition which involves the reactive oxygen species production in the skin of a subject, such as those mentioned above.

In another particular embodiment, the present invention relates to a hydrogel which comprises galactomannan and N-acetyl cysteine, wherein the galactomannan is in the form of a cross-linked matrix and N-acetyl cysteine is incorporated in said cross-linked matrix of galactomannan.

The term "hydrogel" refers to a network of polymer chains which comprises cross-linked galactomannan chains that are water-insoluble but water-swellable, i.e. the water is the dispersion medium.

The hydrogel of the invention provides a reliable and efficient means for delivery N-acetyl cysteine to the site of interest, such as to a wound, ulcer, burn or scald, while improving the antioxidant and healing properties of this active ingredient. Indeed, the experimental tests have shown the antioxidant synergistic effect induced by the combination of a galactomannan, such as locust bean gum, and N-acetyl cysteine over fibroblast cell cultures, improving the cell survival capacity while reducing the intracellular levels of reactive oxygen metabolites. The hydrogel also provides a very good moisture regulation capacity for promoting wound healing.

The hydrogel of the invention comprises polymerized chains of galactomannan, said chains of galactomannan are cross-linked in order to make galactomannan water-insoluble but water-swellable. The cross-linking degree determines the reological properties of the hydrogel, as well as its swellable properties, and allows obtaining a porosity that favors the controlled delivery of N-acetyl cysteine.

Particularly, the galactomannan is selected from the group consisting of guar gum, locust bean gum, cassia gum, tara gum, mesquite gum, fenugreek gum and white clover bean gum. More preferably, the galactomannan is locust bean gum.

In a particular embodiment, galactomannan is cross-linked by means of a cross-linking agent. Chemical agents such as borax (sodium borohydrate), glutaraldehyde and epoxy derivatives can be used. Particularly, the most preferred cross-linking agent is glutaraldehyde.

The cross-linking agent content determines the pore size of the matrix and thus the delivery profile of the active ingredient incorporated therein.

The galactomannan may be present in the hydrogel according to the invention in an amount of at least 50% by weight with respect to the total weight of the hydrogel, preferably at least 75% by weight. More preferably, at least 90% by weight of the hydrogel consists of galactomannan.

The balance of the hydrogel comprises water (up to 20% by weight), the active ingredient (N-acetyl cysteine) and, optionally, salts or other structural compounds which improve the reological properties of the hydrogel.

Among the structural compounds which can be optionally present in the hydrogel, proteins such as collagen, fibronectin, laminin, elastin or combinations thereof, as well as glycosaminoglycans, such as hyaluronates, heparin sulfate or chondroitin sulfate, are preferred.

Preferably, the hydrogel according to the present invention will absorb water or wound fluid and hence become wet, swell or become gelatinous mass but will not spontaneously dissolve or disperse therein. Low solubility renders such materials especially suitable for use as wound dressings to remove reactive oxygen species from the wound fluid.

N-acetyl cysteine may be directly incorporated into the cross-linked galactomannan matrix. This active ingredient may be incorporated by absorption of the agent by the matrix or by adding the agent into the initial formulation for the matrix prior to cross-linking.

In a preferred embodiment of the invention, the incorporation of N-acetyl cysteine into the galactomannan matrix is carried out by the formation of a xerogel.

The term "xerogel" refers to a solid substrate formed from a hydrogel by drying with unhindered shrinkage. It retains high porosity (at least 25%) and enormous surface area (150-900 m$^2$/g) along with very small pore size (1-10 nm).

The obtained xerogel is introduced in an aqueous solution comprising N-acetyl cysteine and then, this active ingredient is gradually incorporated into the porous of the matrix or dispersed therein until the equilibrium is reached.

The N-acetyl cysteine is preferably present in the hydrogel in a concentration ranging from 1 to 10 mM, more preferably from 1 to 5 mM.

Another aspect of the present invention refers to the hydrogel of the invention mentioned above which further comprises curcumin as an additional active ingredient to be incorporated in the matrix of galactomannan. It has been found that the combination of a galactomannan, such as locust bean gum, with N-acetyl cysteine and curcumin provides an even higher synergistic antioxidant effect.

As in the case of N-acetyl cysteine, curcumin may also be incorporated into the galactomannan matrix by absorption of this compound by the matrix or by adding it in the initial formulation for the matrix together with N-acetyl cysteine prior to cross-linking the galactomannan.

However, it is also preferred to incorporate curcumin and N-acetyl cysteine by introducing a xerogel of galactomannan into a solution comprising both active ingredients, thus allowing the gradual incorporation thereof into the matrix of galactomannan.

Curcumin is preferably present in the hydrogel in a concentration ranging from about 1 to about 7.5 µM, more preferably from 1 to 5 µM.

It is to be understood that the active ingredients are incorporated into the hydrogel, so that the agents are released directly from the hydrogel and further delivered via transdermal or transmucosal pathways. The incorporated agents may be released over an extended period of time in order to facilitate wound healing.

In a particular embodiment, once the active ingredient(s) are incorporated and dispersed throughout the matrix of glucomannan, a portion of the agent resides in the matrix while the other portion of the agent is dissolved in the free liquid phase and moves freely through the matrix. Because the agent is dissolved in the free liquid phase, a concentration gradient of the active agent is created between the matrix of the hydrogel and the moisture of the wound itself. Therefore, when the hydrogel is placed onto a moist surface such as an open wound, the soluble agent will move through the free liquid phase toward the agent-free wound moisture, resulting in the delivery of the agent to the wound. This movement of soluble agent further upsets the equilibrium between soluble and insoluble agents, and causes more agent to dissolve into the free liquid phase, thus causing more agent to be delivered to the wound.

Delivery of the active ingredients may also be controlled by the degree of cross-linking in the matrix. The combination of chains cross-linked together creates microcavities wherein the active ingredients are encapsulated. By controlling the amount of cross-linking agent and the length of galactomannan chains, it is possible to regulate the size of the microcavities of the galactomannan matrix. Larger microcavities produced by a lower degree of cross-linking, allow for freer migration and quicker delivery of the active agents, whereas smaller microcavities increase the delivery time.

The process for the preparation of the hydrogel of the invention comprises:
 a) dissolving the galactomannan in an aqueous solution;
 b) subjecting the galactomannan to a chemical cross-linking by adding a cross-linking agent to the aqueous solution of galactomannan to obtain a hydrogel comprising a cross-linked glucomannan matrix;
 c) incorporating N-acetyl cysteine, and optionally the curcumin, into the cross-linked glucomannan matrix.

Preferably, the galactomannan is dissolved in distilled water at room temperature in an amount ranging from 1% to 5% by weight with respect to the total weight of the solution. This solution is maintained under stifling for approximately 2-3 hours. Depending on the galactomannan, it may be required to increase the temperature in order to facilitate the dissolution thereof.

In a particular embodiment, the galactomannan is locust bean gum. In this case, the dissolution should be done at a temperature between 110 and 120° C.

The cross-linking step is carried out with the aim of forming a tridimensional matrix structure, providing it with porous or cavities wherein the active ingredient will be incorporated. Cross-linking methods include UV-induced cross-linking and chemical cross-linking. Chemical agents such as borax (sodium borohydrate), glutaraldehyde, epoxy derivatives and other methods known in the art can be used. UV cross-linking methods require a photoinitiator that initiates the gelling or cross-linking process upon exposure of UV radiation.

The cross-linking degree depends on the amount of cross-linking agent added to the solution and it ranges from about 1% to about 5% by weight with respect to the total weight of the aqueous solution. Preferably, the cross-linking agent is glutaraldehyde.

In a particular embodiment, the solution of galactomannan and the cross-linking agent in maintained under stirring for at least 30 minutes. Subsequently, the solution is poured into molds, maintaining therein until the formation of the hydrogel. The non-reacting cross-linking agent is removed by several washes.

The incorporation of the N-acetyl cysteine, and curcumin when this active ingredient is present in the formulation of the hydrogel, may be done by absorption of the agent by the matrix. Alternatively, the active ingredient(s) may be added to the aqueous solution of galactomannan prior to the cross-linking thereof.

In a preferred embodiment of the invention, the incorporation of the N-acetyl cysteine, and optionally the curcumin, comprises the following steps:
1) drying the hydrogel obtained in step b) to form a xerogel;
2) rehydrating the xerogel by introducing it in an aqueous solution comprising N-acetyl cysteine, and optionally curcumin, to form a hydrogel wherein N-acetyl cysteine, and optionally curcumin, are incorporated into the cross-linked glucomannan matrix.
3) partially drying the hydrogel obtained in step 2).

A dry xerogel or film matrix can be obtained from a hydrogel by a freeze-drying or convective-drying method according to processes known to a person skilled in the art. In a preferred embodiment, the dry xerogel is formed from the hydrogel by evaporative-drying process, preferably air-drying, vacuum-drying or convective-drying.

Subsequently, the xerogel is rehydrated to form a hydrogel which achieves an appropriate release kinetic and, at the same time, a high concentration of active ingredient(s) are incorporated at the release side of the galactomannan matrix.

Finally, the hydrogel is partially drying for its subsequent application to the site of interest.

In a particular embodiment of the invention, the hydrogel further comprises cells incorporated in the matrix of galactomannan or in the surface thereof. The incorporation of cells enhances the regenerative activity of the hydrogel and the tissue repair process in those tissues highly damaged or without the possibility of in situ cellular contribution from the patient, since this biomaterial contains healthy cells of the same type as those present in the damaged tissue.

Preferably, the cells incorporated in the hydrogel are selected from the group consisting of fibroblasts, keratinocytes, endothelial cells, differentiated or undifferentiated mesenchymal stem cells, corneal cells, epithelial cells, cells from leucocitary system, cells from hematopoietic system, differentiated or undifferentiated stem cells, chondrogenic cells, osteoblasts, miocytes, adipocytes and neurons or other cells from the peripheric and central nervous system.

In a particular embodiment of the invention, the hydrogel is incorporated in a wound dressing. Therefore, another aspect of the present invention refers to a wound dressing which comprises the hydrogel of the invention. The wound dressing is preferably in sheet form and comprises an active layer of the hydrogel according to the invention. The active layer would normally be the wound contacting layer in use, but in some embodiments it could be separated from the wound by a liquid-permeable top sheet.

The wound dressing may include other ingredients. For example, in order to decrease the permeability of the wound dressing material, water loss control agents may be added. A decrease in the permeability of the wound dressing material controls the loss of fluids form the wound. Preferred water loss control agents are glycolipids, ceramides, free fatty acids, cholesterol, triglycerides, stearylesters and silicone oil.

If desired, a plasticizer may also be added to the wound dressing. The presently preferred plasticizers are glycerol and water, however, propylene glycol and butanol may also be used.

If desired, a hydration control agent may also be incorporated into the wound dressing material. The preferred hydration control agent is isopropyl alcohol, however, ethanol, glycerol, butanol and propylene glycol may also be used.

Preferably, the wound dressing further comprises a backing sheet extending over the active layer opposite to the wound facing side of the active layer. Preferably, the backing sheet is larger than the active layer such that a marginal region extends around the active layer to form a so-called island dressing. In such cases, the backing sheet is preferably coated with a pressure sensitive medical grade adhesive in at least its marginal region.

Preferably, the backing sheet is permeable to water vapor, but not permeable to liquid water or wound exudates. Preferably, the backing sheet is also microorganism-impermeable. This allows the wound under the dressing material to heal under moist conditions without causing the skin surrounding the wound to macerate.

Suitable polymers for forming the backing sheet include polyurethanes and polyalkoxyalkyl acrylates and methacrylates such as those disclosed in GB-A-1280631.

The adhesive (where present) layer should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631.

The wound facing surface of the dressing is preferably protected by a removable cover sheet. The cover sheet is normally formed from flexible thermoplastic material. Suitable materials include polyesters and polyolefins. Preferably, the adhesive-facing surface of the covers sheet is a release surface. That is to say, a surface that is only weakly adherent to the active layer and the adhesive on the backing sheet, to assist peeling of the adhesive layer from the cover sheet. For example, the cover sheet may be formed from a non-adherent plastic such as a fluoropolymer, or it may be provided with a release coating such as a silicone or fluoropolymer release coating.

Typically, the wound dressing according to the invention is sterile and packaged in a microorganism-impermeable container.

The hydrogel of the present invention may therefore be used on injured tissue and for bodily fluid drainages where control and management of fluid and secretions is desired. The term "bodily fluid" includes, but it is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid and nasal secretions.

In particular, the hydrogel is preferably applicable for usage on exudating acute and chronic wounds for controlling accumulating exudate moisture, support of the wound bed and surrounding tissues.

Accordingly, in an additional aspect, the present invention provides the hydrogel according to the present invention for its use in the treatment and/or healing of acute surgical and traumatic wounds, burns, scalds, fistulas, venous ulcers, arterial ulcers, pressure sores (otherwise known as decubitus ulcers), diabetic ulcers, ulcers of mixed aetiology, and other chronic or necrotic wounds and inflammatory lesions and disorders.

The hydrogel of the present invention is intended for the treatment of both infected and non-infected wounds (that is to say wounds showing no clinical signs of infection). Preferably, the wound is a chronic or necrotic wound. More preferably, the chronic wound is selected from the group consisting of ulcers of venous, arterial or mixed aetiology, decubitus ulcers or diabetic ulcers. Preferably, the hydrogel is used as an antioxidant to reduce oxidative stress in the wound environment and thereby to promote wound healing.

In use, the hydrogel, or the wound dressing containing it, is placed in direct contact with the wound bed. If required, it may be secured into the position with the wound dressing such as that described above. If necessary, the wound dressing and the hydrogel are removed, whereby any accumulated necrotic tissue and exudates is lifted away. The hydrogel may be replaced by a fresh hydrogel and other suitable wound dressing.

The hydrogel may undergo a swelling action as it absorbs exudates moisture, however, they will not dissolve. The swelling action displaces necrotic material from the wound surface and forces the material into the matrix of the hydrogel. The laden moisture content and the retention moisture near the wound bed by the hydrogel contribute to stimulation of the autolytic debridement process whereby the body's own enzymes break-up necrotic tissue and cellular debris.

Another aspect of the present invention refers to a cosmetic composition which comprises galactomannan and N-acetyl cysteine.

The cosmetic composition includes any liquid composition or any composition which comprises the combination of galactomannan and N-acetyl cysteine and which is in the form of gel, cream, ointment or balm for its topical administration. Said compositions are characterized in that they have emollient, protective and healing properties even when they do not have any cosmetically active molecule associated.

In a variant of the invention, the cosmetic composition may also incorporate active molecules, although they do not have any therapeutic effect, they have properties as a cosmetic agent. Among the active molecules which may be incorporated in the antioxidant composition emollient agents, preservatives, fragrance substances, antiacne agents, antifungal agents, antioxidants, deodorants, antiperspirants, antidandruff agents, depigmenters, antiseborrheic agents, dyes, suntan lotions, UV light absorbers, enzymes, fragrance substances, among others, can be cited.

The cosmetic composition may further comprise pH controlling agents, such as, for example, buffer agents, which avoid the pH of the composition reducing to values below 5, as well as preservatives which avoid important structural changes in the composition. A person skilled in the art can determine which additional components can be used and if they are necessary, many of them being in common use in cosmetic compositions.

The cosmetic composition of the invention can be used in the treatment of an age-related skin damage.

The age-related skin damage refers to any skin condition or disorder associated with, caused by, or affected by, intrinsic aging and/or extrinsic aging which are often attributed to damage caused by oxygen free radicals. Oxygen free radicals can damage cells and are believed to accelerate age-related diseases. Age related skin damage can also be caused by years of sun damage, poor nutrition, high stress levels, exposure to environmental pollution, and certain lifestyles choices, such as cigarette smoking, alcohol or drug abuse.

The aging-related skin condition may, for example, involve wrinkles, age spots, sun damage (particularly UV radiation-induced oxidative stress), blemishes, hyperpigmented skin, increased skin thickness, loss of skin elasticity and collagen content and/or dry skin.

In another aspect, the present invention refers to the use the cosmetic composition as described above as an UV-radiation protector.

This invention is further illustrated by the following examples, which are not to be construed in any way as imposing limitations upon the scope thereof.

EXAMPLES

Example 1

Estimation of Limit Concentrations of NAC and Turmeric

N-acetyl cysteine (NAC), locust bean gum (LBG) and curcumin (Turmeric or Tur) were supplied by Sigma.

The limit concentrations in the use of NAC and Turmeric were established after in vitro cytotoxicity and proliferation assays in human fibroblasts within a range from 0.5 mM to 20 mM for NAC and from 0.5 µM to 50 µM for turmeric.

The proliferation assay was carried out using the MTT colorimetric assay (Roche 11465007001). MTT is a yellow tetrazolium salt which forms formazan crystals in active cells. The formazan crystals are solubilized and the resulting color is quantified by means of spectrophotometry at 550 nm.

Fibroblasts were seeded in a 96-well plate at a density of 4000 cells per well. The cells were maintained at 37° C. in an incubation stove. The following day, the treatments of NAC and Turmeric were added to the cell culture using a volume of 200 µL per well. The cell culture was left to incubate for 24, 48 and 72 hours.

After each incubation time, 20 µL of MTT (a final concentration of 0.5 mg/mL) were added to each well. The plate was maintained for 4 hours in the incubation stove in order to allow the formation of formazan crystals. Subsequently, 100 µL of solubilizer was added to each well and the plate was left in the incubation stove until the following day. Then, the data of absorbance at 550 nm were measured.

Figure 2:
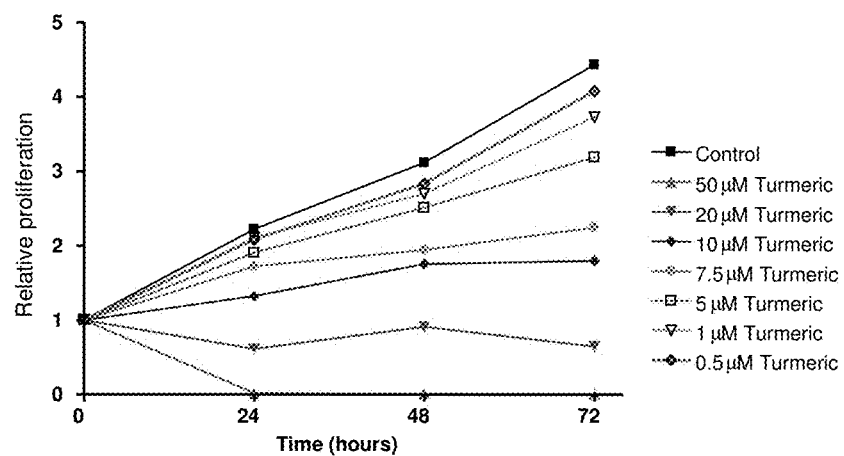
FIG. 2 shows: (a) the results of cell proliferation in fibroblasts by means of the MTT colorimetric assay, using different concentrations of turmeric, and (b) the $IC_{50}$ values with respect to the control.
Figure 2:
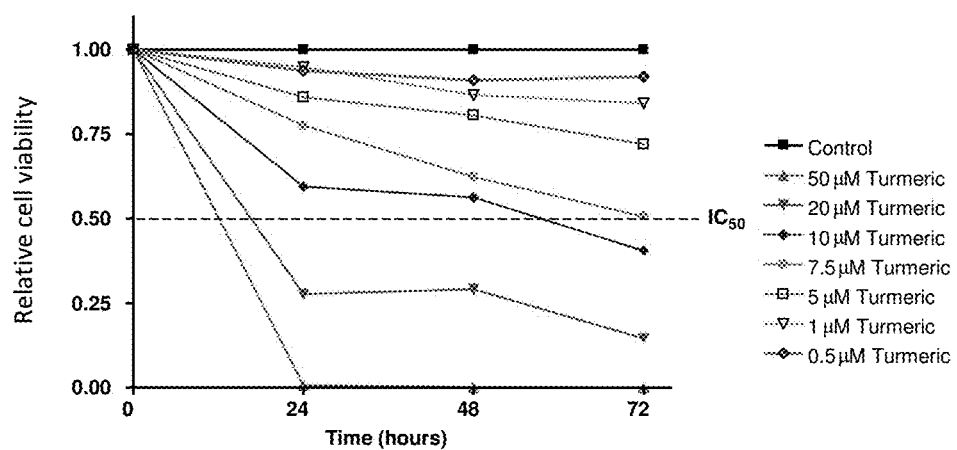

FIGS. 1a and 2a show the results from cytotoxicity and proliferation assays by means of the MTT colorimetric assay, using different concentrations of NAC and turmeric.

The $IC_{50}$ of each component, i.e. the concentration causing a 50% cell decrease with respect to the control, was established as the toxicity limit (FIGS. 1b and 2b).

For the case of NAC, none of the concentrations studied reached $IC_{50}$ at 72 hours, although concentrations of 10 and 20 mM progressively reduced cell proliferation with respect to the control. The maximum limit of concentration of NAC could be established at 10 mM. Based on the results obtained in the experiments, concentrations of 1 and 5 mM of NAC were selected since they resulted in an improvement of the proliferative rate in the fibroblasts.

In the case of the study of the maximum limit of concentration of turmeric, it was observed how the concentrations of 20 and 50 µM have toxicity from the first 24 hours, exceeding the $IC_{50}$ limit. The concentration of 10 µM exceeds the limit at 72 hours and the concentration of 7.5 µM reaches the $IC_{50}$ at 72 hours. Therefore, the concentration of 7.5 µM can be established as the maximum limit of use of turmeric in the mixture.

Concentrations of 1 and 5 µM of Turmeric were selected for the experiments since no toxic effects were observed.

Example 2

Effect of the Components of the Composition of the Invention and the Combination Thereof on the Viability of Human Fibroblasts The objective of the assay is to determine the effect caused by LBG, NAC, turmeric and combinations thereof on the survival capacity of the cells in an adverse environment, such as the one in the bed of a wound.

To that end, fibroblasts were subjected to an oxidative environment using hydrogen peroxide for 1 hour and were put in contact with LBG, NAC, turmeric and combinations thereof. The cell viability of fibroblasts in culture was analyzed by means of the MTT colorimetric assay as defined above.

Cell Seeding for the Assay

The day before the assay, the fibroblasts were seeded in a 96-well plate at a density of 11500 cells per well. All the assays were performed in triplicate.

Assay

The treatments were prepared on the day of the experiment and the hydrogen peroxide was added just before the assay.

Preparation of the 1% Locust Bean Gum in Normal Cell Growth Medium

A solution of locust bean gum of 1% in distilled water was prepared and heated above 100° C. until completing dissolution of the gum. The solution was then centrifuged for 20 minutes at 4000 rpm to remove the impurities from the mixture. The solution of the locust bean gum was lyophilized. The liophilisate was dissolved in cell growth medium (DMEM+10% FBS) at a concentration of 1%.

Preparation of the NAC and Curcumin Treatments and of Hydrogen Peroxide

The NAC and curcumin treatments and the hydrogen peroxide were prepared just before starting the assay. To prepare the curcumin stock, it is necessary to know the purity of the Turmeric batch available and readjust the calculation to add the necessary concentration.

The treatments and the hydrogen peroxide were added at the same time and left to incubate for 1 hour.

After the incubation, the treatments were eliminated from the cells and normal growth medium and 10% MTT added. The solubilizer was added at 4 hours.

Then, the data of absorbance at 550 nm were measured.

To study the synergistic or additive effect of the combination of the components, the results were analyzed by means of applying the formulas specifically designed to study these parameters:

A. Adapted Formula of the Dose-Modifying Factor (DMF), Referred to as Combination Factor (CF).

The original formula analyzes the dose-modifying factor taking as data the percentage of cell inhibition caused by two drugs administered alone and in combination (Thrall B D et al. Differential sensitivities of murine melanocytes and melanoma cells to buthionine sulfoximine and anticancer drugs. *Cell. Res.* 1991; 4: 237-9). Said formula has been used and published in subsequent international articles of our research group.

The formula presented herein is adapted from the one indicated above, taking as a reference the increase in the percentage of surviving cells with respect to the oxidized control, and is as follows:

$$CF = \frac{\% \text{ protection } LBG + NAC}{(\% \text{ protection } LBG) + (\% \text{ protection } NAC)}$$

$$\% \text{ protection} = \left\{ \frac{\text{Treated value}}{\text{Oxidized control value}} \times 100 \right\} - 100$$

B. Original Formula Referred to as Combined Index (CI)

The formula presented herein is an original formula of one of the authors of the patent (T. Palomares) which analyzes the percentage of surviving cells in the presence of an agent, alone or in combination with others, over the number of original cells by subtracting the number of surviving cells from the oxidized control. Thus, the increase in the number of surviving cells with respect to the cells that are not treated and exposed to the oxidant is analyzed. The formula is as follows:

$$CI = \frac{(\% \ Cs \ LBG + NAC) - (\% \ Cs \ Cox)}{(\% \ Cs \ LBG - \% \ Cs \ Cox) + (\% \ Cs \ NAC - \% \ Cs \ Cox)}$$

Cox: oxidized control
Cs: surviving cells with respect to the initial control without oxidation In both formulas, a value >1 indicates a synergistic effect (with higher significance the greater said value is) and <1 indicates an additive effect with has a higher value the closer it is to 1.

Once the appropriate numerical verifications have been made, identical results are obtained with both formulas.

Figure 3:
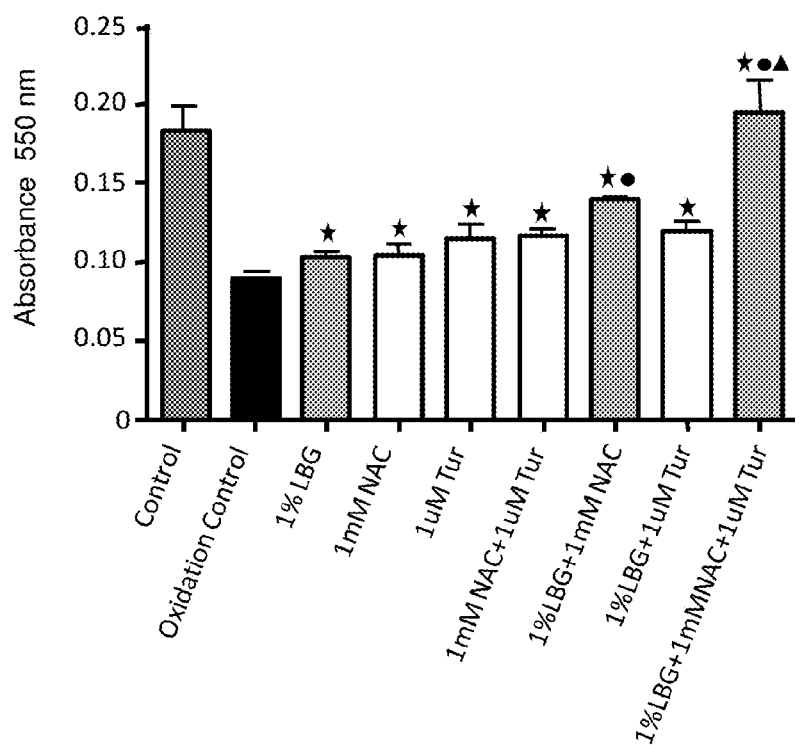
FIG. 3 shows the results corresponding to the MTT colorimetric assay when a fibroblasts culture is subjected to an oxidative environment and when it is put in contact with 1% LBG, 1 mM NAC, 1 μM Turmeric and combinations thereof.

The results corresponding to the analysis of the experiments in which the cells were subjected to an oxidative environment (1 mM $H_2O_2$) and treated with 1% LBG, 1 mM NAC, 1 mM Turmeric and combinations thereof are shown in FIG. 3. The experimental data were obtained 1 hour post-oxidation. These data indicate that the triple combination LBG+NAC+Tur produces the best protection effect, reaching control levels. The combination LBG+NAC increase also the cell viability with respect to oxidized control and with respect to LBG, NAC, Tur, LBG+Tur and NAC+Tur treatments.

Table I shows the percentage of viability of the cells subjected to oxidative stress with respect to the non-oxidized control group.

| Oxidation 1 mM $H_2O_2$ | | |
| --- | --- | --- |
| TREATMENTS | Absorb | % Viability |
| Control | 0.18 | 100 |
| Oxidation control | 0.09 | 48.8 |
| 1% LBG | 0.1 | 56.59 |
| 1 mM NAC | 0.1 | 57.14 |
| 1% LBG + 1 mM NAC | 0.14 | 77.77 |
| 1 μm Turmeric | 0.12 | 63.18 |
| 1 mM NAC + 1 μm Turmeric | 0.12 | 64.28 |
| 1% LBG + 1 mM NAC + 1 μm Turmeric | 0.2 | 100 |

Table II shows the indices obtained by means of applying formulas A and B in which it is concluded that there is a synergistic effect in the combinations of LBG+NAC and the triple combination of LBG+NAC+Turmeric.

| Treatment | Value | Effect |
| --- | --- | --- |
| 1% LBG + 1 mM NAC | 1.69 | Synergistic |
| 1% LBG + 1 μM Tur | 0.75 | Additive |
| 1 mM NAC + 1 μMTur | 0.67 | Additive |
| 1% LBG + 1 mM NAC + 1 μm Tur | 1.85 | Synergistic |

The results have pointed out that the combinations of LBG, either with NAC or with NAC+Tur, cause a synergistic effect in the increase of cell viability in a oxidative stress situation. However, the combination of LBG+Tur and NAC+Tur produces the expected additive effect.

The analysis of the most pronounced protection effects show that the combination of the three agents results in the greatest protective effect (100% of surviving cells). The combination of the three agents shows an effect that is 1.3 times greater than the treatment with LBG+NAC (77.77%).

Example 3

Effect of the Components of the Composition of the Invention, Alone or in Combination, on the Decrease of the Oxygen Reactive Metabolites Generated in the Human Fibroblasts Subjected to an Oxidative Environment The increase of reactive oxygen metabolites (ROMs) is one of the main causes hindering the healing of a wound. This effect contributes to the loss of proliferative capacity of the cells and to the increase in the expression of metalloproteases, which degrade the new dermal matrix formed and prevent healing.

To quantify the ROM-decreasing or antioxidant capacity of LBG, NAC and turmeric, the production of the ROMs generated upon oxidizing a culture of fibroblasts with a high concentration of hydrogen peroxide was measured.

The intracellular ROMs were quantified by means of the labeling thereof with the fluorescent probe 2',7'-dichlorofluorescein diacetate (Molecular Probes D399). This probe is capable of emitting fluorescence at 538 nm when it is oxidized with reactive oxygen metabolites. The cell oxidation was carried out with 1 mM hydrogen peroxide.

Cell Seeding for the Assay

The day before the assay, the fibroblasts were seeded in a 96-well plate at a density of 11500 cells per well. All the assays were performed in triplicate.

Assay

The treatments were prepared on the day of the experiment and the hydrogen peroxide was added just before the assay.

Preparation of the 1% Locust Bean Gum in Normal Cell Growth Medium

A solution of locust bean gum of 1% in distilled water was prepared and heated above 100° C. until completing dissolution of the gum.

The solution was then centrifuged for 20 minutes at 4000 rpm to remove the impurities from the mixture. The solution of the locust bean gum was lyophilized. The lyophilisate was dissolved in cell growth medium (DMEM+10% FBS) at a concentration of 1%.

Labeling the Cells with the Fluorescent Probe

Before adding the treatments and the hydrogen peroxide, the cells were labeled with the fluorescent probe at a concentration of 50 μM for 30 minutes in darkness.

Preparation of the NAC and Turmeric Treatments and of Hydrogen Peroxide

The NAC and Turmeric treatments and the hydrogen peroxide were prepared just before starting the assay. To prepare the turmeric stock, it is necessary to know the purity of the Turmeric batch available and readjust the calculation to add the necessary concentration.

After labeling the cells, the antioxidant treatments and the hydrogen peroxide were added.

The fluorescence emitted at 538 nm by the probe was collected 20 minutes after the start of the oxidation.

Figure 4:
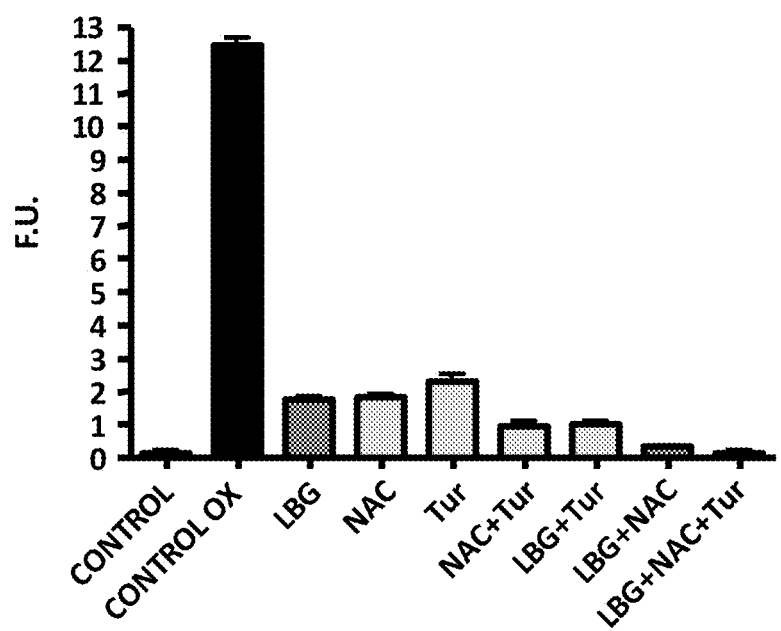
FIG. 4 shows the intracellular ROM levels of fibroblasts subjected to an oxidative environment using 1 mM of $H_2O_2$, by means of the fluorescence units obtained in the labeling with the probe 2',7'-dichlorofluorescein diacetate and when fibroblasts are put in contact with 1% LBG, 5 mM NAC, 5 μM Turmeric and combinations thereof.
Figure 5:
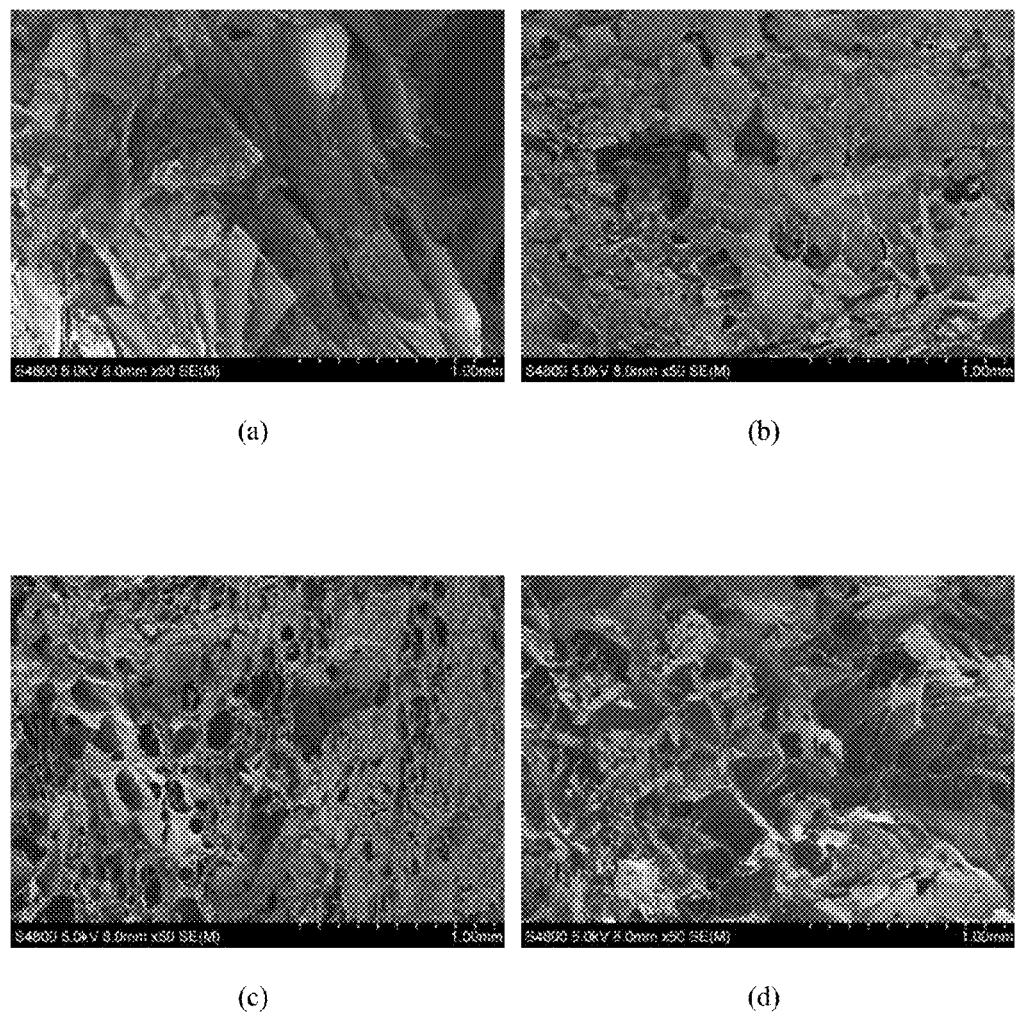
FIG. 5 shows photographs taken from scanning electron microscope (SEM) of a hydrogel of locust bean gum cross-linked with glutaraldehyde at: (a) 0% wt; (b) 0.5% wt; (c) 1% wt and (d) 2.5% wt.

FIG. 4 shows the intracellular ROM levels of the fibroblasts subjected to an oxidative environment using 1 mM of $H_2O_2$, by means of the fluorescence units obtained in the labeling with the probe 2',7'-dichlorofluorescein diacetate and also when fibroblasts are put in contact with 1% LBG, 5 mM NAC, 5 μM Turmeric and combinations thereof.

Table III shows the data of the percentage of decrease of ROMs with respect to the oxidized control, when the cells were subjected to 1 mM of hydrogen peroxide and in contact with the components of the composition of the invention.

| | 1 mM $H_2O_2$ | |
| --- | --- | --- |
| | F.U. | % decrease of ROS |
| CONTROL | 0.157 | |
| OXIDIZED CONTROL | 12.47 | |
| LBG | 1.74 | 86 |
| NAC | 1.82 | 85 |
| Tur | 2.31 | 81 |
| NAC + Tur | 0.97 | 92 |
| LBG + Tur | 1 | 91 |
| LBG + NAC | 0.307 | 97 |
| LBG + NAC + Tur | 0.157 | 99 |

As can be observed, there is a significant decrease of the intracellular ROM levels in the cells which are in contact with LBG, NAC, Turmeric and combinations thereof.

The addition of NAC to the solution of LBG causes a significant decrease of the intracellular ROM levels with respect to the LBG alone.

However, the triple combination LBG+NAC+Tur produces the highest benefit in terms of the decrease of the intracellular ROM levels, which are similar to those of the control group (without oxidation).

In order to verify the synergistic or additive effect of the combination of the different components, the results were analyzed by applying formulas A and B mentioned in example 2. However, in this case the decrease in intracellular ROM levels was taken as a reference with respect to the oxidized control.

The results are shown in Table IV:

| Treatments | Value | Effect |
| --- | --- | --- |
| LBG + NAC | 3.29 | Synergistic |
| LBG + Tur | 0.65 | Additive |
| NAC + Tur | 0.68 | Additive |
| 1% LBG + 1 mM NAC + 1 µM Tur | 3.30 | Synergistic |

The application of formulas A and B show clearly a synergistic effect produced by the LBG+NAC and LBG+NAC+Tur combinations, whereas the LBG+NAC and NAC+Tur combinations produce and additive effect, with respect to intracellular ROS reduction.

Example 4

Preparation of a Hydrogel of Locust Bean Gum with N-acetyl Cysteine Incorporated Therein A weighed amount of locust bean gum was dispersed in distilled water to form a solution containing 1-5 wt % of said gum. In order to favor the synthesis of the hydrogel, sulfuric acid was added to the solution until obtaining a pH of 2, with the aim of protoning hydroxyl groups of the locust bean gum. The solution was stirred at room temperature for 2-3 hours and, subsequently, the temperature was raised until 100-120° C. At this temperature, the solution was stirred for at least 30 minutes.

The solution was centrifuged at 4000 rpm for 20 minutes in order to remove impurities in the mixture, thus the pure locust bean gum solution is in the supernadant and the impurities are deposited in the pellet.

The locust bean gum solution was subjected to a chemical cross-linking step using glutaraldehyde as cross-linking agent. For this purpose, glutaraldehyde was added to the solution of locust bean gum while stirring for at least 30 minutes. The amount of glutaraldehyde depends on the desired final characteristics of the hydrogel. If a quick delivery of the N-acetyl cysteine is required, lower quantities of cross-linking agent are added to the solution of locust bean gum in order to obtain a low cross-linking degree. On the contrary, if an increased delivery time of N-acetyl cysteine is required, high quantities of cross-linking agent are added to the solution of locust bean gum in order to obtain a high cross-linking degree. FIGS. 5a-5d correspond to photographs taken from scanning electron microscope (SEM) which show the increase in the porosity degree of a hydrogel of locust bean gum at 3% by weight when increasing the concentration of the cross-linking agent from 0 to 2.5% by weight.

The mixture of locust bean gum and glutaraldehyde was placed on petri dishes. The cross-linking reaction was carried out at 37° C.

Once the hydrogel has been formed, it was washed with sodium bisulfate (Sigma 13438) at 5% and then with distilled water, in order to remove the non-reacted glutaraldehyde. Subsequently, the hydrogel was dried in an oven at 65° C. to form a xerogel.

In order to incorporate the N-acetyl cysteine into the structure of the locust bean gum, the xerogel was rehydrated by introducing it into a saturated solution of N-acetyl cysteine and PBS. Finally, the obtained hydrogel was partially dried for its subsequent use.

Example 5

Assessment of the Effect of a Hydrogel Containing LBG, LBG+NAC, and LBG+NAC+Tur, on the Wound Healing Process in the Pig Skin Four male pigs of 25-35 kg body weight were selected. Before starting the procedure, the animals were submitted to 1 week acclimatization period.

Preoperatively, the animals were sedated with intramuscularly azaperone (4 mg/kg)+ketamine (10 mg/kg) and tracheally intubated and analgesia was induced with intravenous buprenorfine (0.01 mg/kg). Anaesthesia was induced and maintained with propofol (4 mg/kg), isoflurane (1.5-2%, oxygen). Presurgical antibiotherapy was performed with intravenous cephalotin (22 mg/kg).

Four skin lesions were surgically generated in the dorsal area of each pig. Three different biomaterial matrix combinations (LBG, LBG+NAC and LBG+NAC+Tur) were applied in three of the four lesions and saline was applied in the control lesion. The dressings were replaced every 3 days when wounds were cleaned and dressing changed.

In the postoperative period, a macroscopic evaluation of tissue healing was performed throughout the experiment. Biopsies for histological evaluation were obtained 5, 10 and 15 days after lesions generation. All skin biopsy samples were fixed in 10% neutral buffered formalin, routinely processed and stained with hematoxylin and eosin (H&E) for histopathological study. Histopathological evaluation in treated and control areas was performed. Parameters such as epidermis reepitelization, presence of dermal inflammation and fase of granulation tissue formation and maduration were assessed.

The results show the faster evolution from the initial days, mainly in LBG+NAC and LBG+NAC+Tur treated lesions. Furthermore, the microscopic analysis showed an improvement in the granulation tissue formation and in the maduration of this tissue with respect to control lesion.

Figure 6:
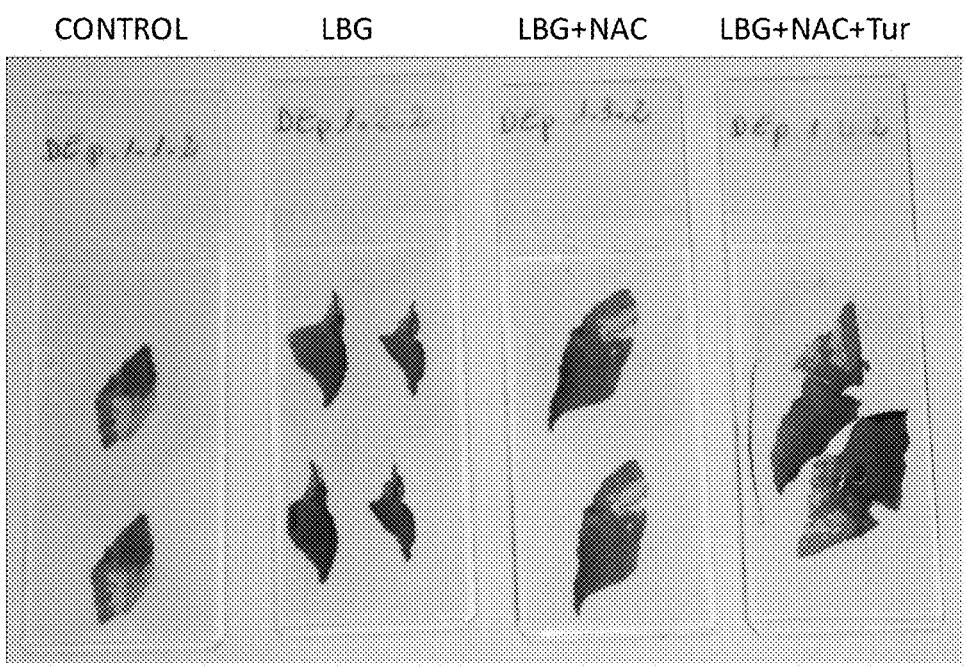
FIG. 6 shows a macroscopic view of a 10-days evolution biopsy of skin lesions surgically generated in the dorsal area in a healing animal model in pigs.

FIG. 6 shows a macroscopic view of a 10 days of evolution biopsy, wherein it can be observed an increase in the new tissue formation in the treated groups, but particularly in the group treated with a LBG+NAC+Tur.

When calculations of wound surface were performed in the three groups, an improvement in the wound closure capacity was shown in the three groups. However, this effect was increased in LBG+NAC group and the higher effect was observed in the LBG+NAC+Tur group.

Table V shows the estimated lesion area in the different treated groups and the index that indicates the capacity of wound reduction presented by these groups. The index also indicates that the higher effect was achieved by LBG+NAC+Tur treatment.

| | Lesion area (cm$^2$) | Lesion area reduction index (relative to control group) |
| --- | --- | --- |
| Control | 7 | 1 |
| LBG | 5.88 | 1.2 |
| LBG + NAC | 4.62 | 1.5 |
| LBG + NAC + Tur | 3.78 | 1.85 |

Figure 7:
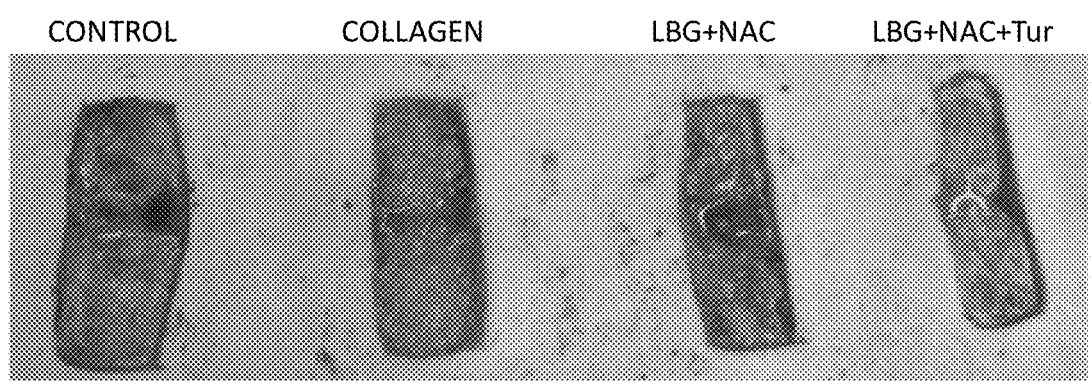
FIG. 7 shows a 3-days evolution photograph of skin lesions surgically generated in the dorsal area in a healing animal model in pigs.

FIG. 7 shows a three days evolution photograph where treatments with LBG+NAC and LBG+NAC+Tur were compared with an established collagen treatment. As can be observed, there is a reduction in lesion area in both LBG+NAC and LBG+NAC+Tur groups with respect to control and collagen treated group, and again the LBG+NAC+Tur presented the higher area reduction and the best quality healing process.

The invention claimed is:
1. An antioxidant composition comprising galactomannan, N-acetyl cysteine, and curcumin.
2. The composition as defined in claim 1, further comprising cosmetically acceptable components.

* * * * *